US00PP08909P

United States Patent [19]

Walters, deceased

[11] Patent Number: Plant 8,909

[45] Date of Patent: Sep. 20, 1994

[54] VARIETY OF GERANIUM NAMED BARON

[75] Inventor: Ernest Walters, deceased, late of Hucknall, England, by Mary Bodill, administratrix

[73] Assignee: Oglevee, Ltd., Connellsville, Pa.

[21] Appl. No.: 182,498

[22] Filed: Jan. 14, 1994

[51] Int. Cl.[5] ..... A01H 5/00

[52] U.S. Cl. ..... Plt./87.12

[58] Field of Search ..... Plt. 87.12

*Primary Examiner*—James R. Feyrer

*Attorney, Agent, or Firm*—Webb Ziesenheim Bruening Logsdon Orkin & Hanson

[57] ABSTRACT

This new variety of Regal geranium has a very dark purple flower edged in white above medium green foliage. It roots easily and quickly; produces many cuttings; flowers abundantly over a long period of time but is slow to shatter.

1 Drawing Sheet

BACKGROUND OF THE INVENTION

The present invention comprises a new and distinct cultivar of *Pelargonium*×*domesticum* known by the varietal name 'Baron' (Oglevee No. 516; 'Walters Pride', No. 45). The new variety was discovered in a selected breeding program in Hucknall, Nottingham, Great Britain in the early to mid 1980's. The parentage of the new variety is not known with certainty but the breeding program of Ernest Walters, deceased, which extended more than 30 years, is disclosed in a Walters article published in Vol. 110, Part 8, August 1985, Journal of The Royal Horticultural Society. The new variety was first received in the United States in 1987 and was asexually reproduced by cuttings at Oglevee, Ltd. in Connellsville, Pa. in 1987. The new variety has been asexually reproduced by cuttings at Oglevee Ltd. in Connellsville, Pa. over a several year period. It has also been trial and field tested at Connellsville and has been found to retain its distinctive characteristics through successive propagations.

The cultivar when grown in a glass greenhouse in Connellsville, Pa. using natural light and 60° F. night, 68° F. day and 71° F. vent, has a response time of 14 weeks from a rooted cutting to flowering in a 6 inch pot. The response time was determined on plants grown in soilless media employing constant fertilizer 150–200 parts per million of nitrogen and potassium in full light. The rooted cuttings were potted on Nov. 2, 1992 and flowered on Feb. 8, 1993.

DESCRIPTION OF THE DRAWINGS

The top photograph of the accompanying photographic drawing illustrates the inflorescence of the new cultivar, the color being as nearly true as possible with color illustrations of this type.

The bottom photograph of the accompanying photographic drawing illustrates the entire plant of the new cultivar, the color being as nearly true as possible with color illustrations of this type.

DESCRIPTION OF THE NEW PLANT

The following detailed description sets forth the characteristics of the new cultivar. The data which defines these characteristics were collected by asexual reproductions carried out by Oglevee Ltd. in Connellsville, Pa. The plant history was taken on six week plants blossomed under natural light in a greenhouse and the color readings were taken indoors under 200–220 foot candles of fluorescent cool white light. Color references are primarily to The RHS Color Chart of The Royal Horticultural Society of London.

THE PLANT

Classification:

*Botanical.*—*Pelargonium*×*domesticum.*

*Commercial.*—Regal geranium.

Form: Upright mound shaped habit.

*Height.*—24–26 cm from medial surface.

*Growth.*—Strong, controlled.

Strength: Fast rooting, prolific flowering.

Foliage: Stalked leaf attachment.

Leaves:

*Size.*—7.5–8.0 cm across at widest point.

*Shape.*—Depressed ovate; Base: Truncate.

*Margin.*—Serrately lobed.

*Texture.*—Leathery; slightly pubescent.

*Color.*—Top: Yellow/Green Group 147B. Bottom: Yellow/Green Group 146B.

*Ribs and veins.*—Palmate venation. Color: Yellow/Green Group 146C.

Petioles:

*Color.*—Yellow/Green Group 146C.

*Length.*—4.0 to 7.5 cm.

Stem:

*Color.*—Yellow/Green Group 146C.

*Internodes.*—1.0–3.0 cm in length.

THE BUD

Shape: Elliptical.

Size: 1.5–2.0 cm in length; bud just showing color.

INFLORESCENCE

Blooming habit: Many small florets opening slowly to eventually form a full long lasting flower head.

*Size.*—9.0–9.5 cm across.

*Borne.*—Umbel; florets on pedicel; pedicel on peduncle.

Florets:

*Form.*—Cupped.

*Color.*—Top: Outside margin Purple Group 76D. Blotch Purple Group 79A, distinct ring around blotch Purple Group 78A.

*Petals.*—Single; not united; margin entire; 5 in number.

*Size.*—4.0–5.0 cm across.

*Texture and appearance.*—Smooth; appearance from a distance is a very dark purple flower edged in white above medium green foliage.

Petaloids:

*Quantity.*—None.

Pedicel:

*Length.*—1.5–2.0 cm.

*Color.*—Yellow/Green Group 146D.

Peduncle:

*Length.*—3.5–5.0 cm.

*Color.*—Yellow/Green Group 146C.

Disease resistance: Not known.

Lasting quality: Continuous blooming; slow to shatter.

REPRODUCTIVE ORGANS

Stamens:

*Anthers.*—3.0–4.0 mm in length.

*Filaments.*—1.5–2.0 cm in length. Color: White.

*Pollen.*—Golden Brown.

Pistils:

*Number.*—One.

*Length.*—1.5–2.0 cm in length.

*Stigma.*—5–7 parted. Color: Red/Purple Group 60C.

*Style.*—1.3–1.4 cm in length. Color: Red/Purple Group 60C.

Ovaries: Lt. green in color; very pubescent; 5.0–6.0 mm in length.

Fruit: None observed.

GENERAL CHARACTERISTICS

This new variety of Regal geranium has a very dark purple flower edged in white above medium green foliage. It roots easily and quickly; produces many cuttings; flowers abundantly over a long period of time but is slow to shatter.

It is claimed:

1. A new and distinct variety of geranium plant substantially as shown and described.

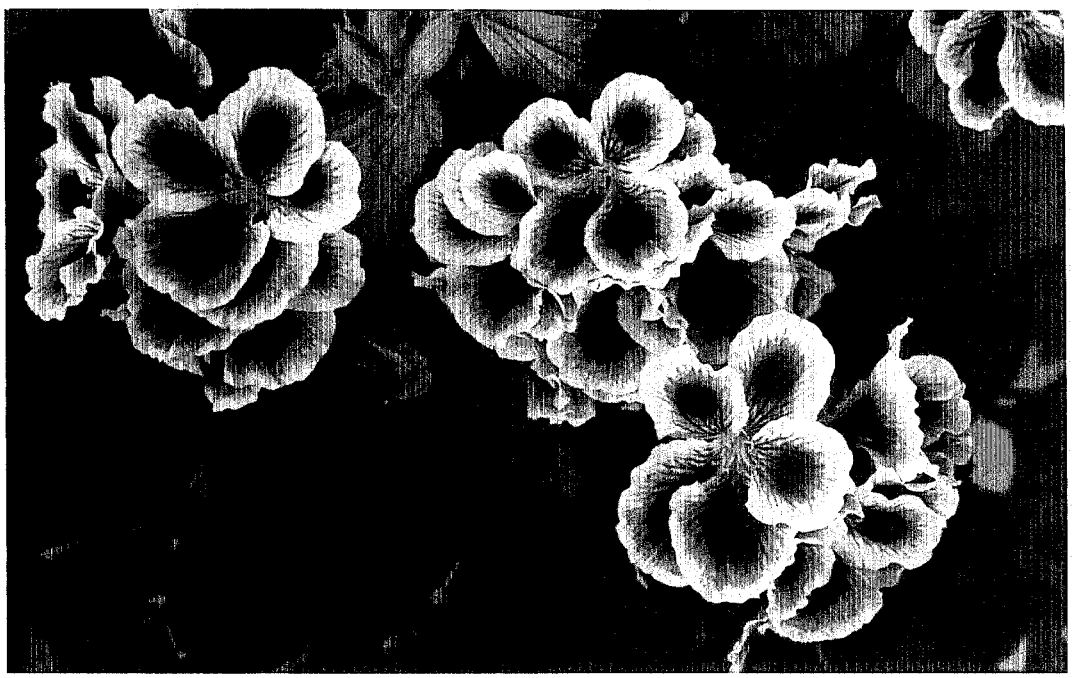
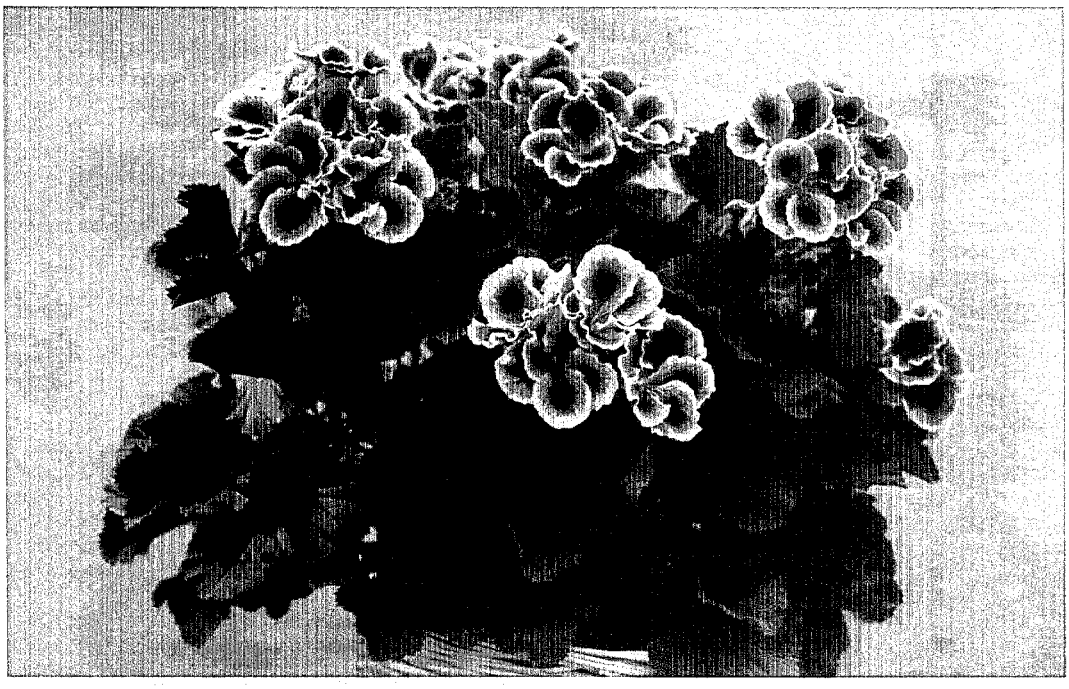

* * * * *